United States Patent
Kobori et al.

(10) Patent No.: US 7,442,498 B2
(45) Date of Patent: Oct. 28, 2008

(54) METHOD OF EXAMINING SPECIMEN AND SPECIMEN CONTAINER TO BE USED IN THE EXAMINATION METHOD

(75) Inventors: Kiichiro Kobori, Ryugasaki (JP); Michiko Kawamoto, Ryugasaki (JP); Koji Ushizawa, Ryugasaki (JP)

(73) Assignee: Daiichi Pure Chemicals Co., Ltd., Tokyo (JP)

( * ) Notice: Subject to any disclaimer, the term of this patent is extended or adjusted under 35 U.S.C. 154(b) by 0 days.

(21) Appl. No.: 10/546,691

(22) PCT Filed: Mar. 9, 2004

(86) PCT No.: PCT/JP2004/003025

§ 371 (c)(1), (2), (4) Date: Jul. 10, 2006

(87) PCT Pub. No.: WO2004/081568

PCT Pub. Date: Sep. 23, 2004

(65) Prior Publication Data

US 2007/0015140 A1 Jan. 18, 2007

(30) Foreign Application Priority Data

Mar. 10, 2003 (JP) ............................ 2003-063832

(51) Int. Cl.
- *C12Q 1/70* (2006.01)
- *C12Q 1/00* (2006.01)
- *G01N 55/543* (2006.01)
- *G01N 55/553* (2006.01)
- *G01N 31/00* (2006.01)

(52) U.S. Cl. .......................... 435/5; 436/525; 436/535; 422/56; 422/58; 422/61

(58) Field of Classification Search .................. None
See application file for complete search history.

(56) References Cited

U.S. PATENT DOCUMENTS 4,874,691 A 10/1989 Chandler

FOREIGN PATENT DOCUMENTS

CN 86103715 4/1987

(Continued)

OTHER PUBLICATIONS

International Search Report for PCT/JP2004/003025 dated Mar. 26, 2004.

(Continued)

*Primary Examiner*—Mary E. Mosher
*Assistant Examiner*—Stuart W Snyder
(74) *Attorney, Agent, or Firm*—Sonnenschein Nath & Rosenthal LLP

(57) ABSTRACT

A method of immunologically examining a specimen which comprises attaching a cap having a filter impregnated with a labeled antibody enclosed therein to a container body containing a diluted liquid specimen, pouring the diluted liquid specimen from the container into a test device, observing the reaction and thus examining the presence or absence of an analyte in the specimen. This examination method, whereby effects of differences among individual operators can be minimized and the occurrence of a nonspecific reaction can be prevented, is highly excellent in the reproducibility of the examination results and storage stability of a test reagent. A specimen container to be used in the above method to which a cap having a filter impregnated with a labeled antibody enclosed therein is attached. This container is appropriately usable as a member constituting a simplified diagnosis kit.

7 Claims, 1 Drawing Sheet

FOREIGN PATENT DOCUMENTS

| | | |
|---|---|---|
| EP | 0312394 | 4/1989 |
| EP | 1081496 | 3/2001 |
| EP | 0687910 | 7/2007 |
| JP | 1229969 | 9/1989 |
| JP | 06-167497 | 6/1994 |
| JP | 06-273419 | 9/1994 |
| JP | 06-308126 | 11/1994 |
| JP | 07-260777 | 10/1995 |
| JP | 08-082622 | 3/1996 |
| JP | 2001-124775 | 5/2001 |
| JP | 2003-500651 | 1/2003 |
| WO | WO9218844 | 7/2007 |

OTHER PUBLICATIONS

European Search Report Corres. to EP Ser. No. 04718761; Jul. 9, 2007.

Chinese Examination Report corresponding to Chinese Ser. No. 2004800006372.X; Mar. 9, 2007.

METHOD OF EXAMINING SPECIMEN AND SPECIMEN CONTAINER TO BE USED IN THE EXAMINATION METHOD

Related Applications

This application is the National Stage of PCT/JP2004/003025 under 35 USC §371 which claims priority under 35 U.S.C. §119 to Japanese Application No. 063832/2003 filed Mar. 10, 2003, the entirety of which is incorporated herein by reference.

TECHNICAL FIELD

The present invention relates to a method of determining the presence or absence of an analyte in a specimen in an immunological assay using an antigen-antibody reaction and to a specimen container to be used in such an examination method. Specifically, the present invention relates to a novel determination method by which the presence or absence of an analyte in a specimen in an examination method adapting an immune reaction by an antigen-antibody can be examined simply and quickly and to a novel specimen container to be used in such an examination method.

BACKGROUND ART

An immunological examination method using an antigen-antibody reaction has been widely applied in various clinical examinations. A typical procedure thereof is to bring a specimen such as blood, urine, sputum, saliva, and nasal discharge or a specimen-diluted solution thereof into contact with a labeled-antibody solution in which antibody is labeled with a coloring identification material such as an enzyme, noble metal colloid, stained latex, and pigment to allow the antigen in the specimen to specifically react with the labeled antibody to make an antigen-antibody immune complex, followed by determining the amount of the immune complex through visual observation or as an optical change to conduct a qualitative or quantitative determination of antigen in the specimen.

Various simplified diagnostic kits adapting the above examination method have been developed and commercially available as tools for simply and quickly carrying out examination and diagnosis with respect to virus infection, pregnancy judgment, identification of cancer disease. As an example thereof, the current situation of a simplified diagnostic kit for examination and diagnosis for influenza virus infection will be described.

Reagents and tools for simply and quickly diagnosing influenza virus have been rapidly put to practical use because therapeutically effective anti-virus pharmaceutical preparations have become applicable recently in addition to avoiding needless administration of the conventional antibiotics and analgesics. Therefore, simplified diagnostic kits based on ELISA (enzyme-linked immunosorbent assay) have been developed and available from various pharmaceutical companies. One of their examples is disclosed in JP-A-2001-124775 and JP-A-2000-230931. Since medicines effective to influenza A virus and influenza B virus, respectively, have appeared, test reagents and tools capable of identifying and discriminating the types A or B have been developed. As the representative example, the usage of a simplified diagnostic kit for the influenza infection which uses a colloidal gold labeled antibody solution will be described as follows. (Reference Example 1)

<Usage of Simplified Diagnostic Kit for Influenza Infection Using Conventional Colloidal Gold Labeled Antibody Solution (Sandwich Type Simplified Measurement Method Using Flow-Through Technique)>

A. At first, a specimen which is collected as nasal discharge or a wipe liquid from the nasal cavity is added to a dilute solution prepared by adding a surfactant to a buffer solution, followed by stirring. The resulting mixture, as a diluted liquid specimen (a pre-treated specimen solution), is filled in a first tubular container with the end thereof covered with a cap having a built-in filter.

B. The diluted liquid specimen is transferred from the first tubular container to a second tubular container through the filter of the cap, and several droplets of a suspension of colloidal gold labeled anti-influenza antibody (a colloidal gold labeled antibody solution) are then dropped into the second container, followed by mixing them well to form a complex of the influenza virus in the specimen and the colloidal gold labeled anti-influenza antibody. The second tubular container is provided with a filtered cap different from the one used in the above step A and then left to stand for 2 to 5 minutes.

C. The whole amount of the mixture in the second tubular container is injected into a test device (a device for immunoassay) filled with a carrier (a porous film material such as a membrane) on which anti-influenza antibody is immobilized and an absorbent (such as absorbent cotton or absorbent paper) to allow the carrier to adsorb the complex of the influenza virus in the specimen and the colloidal gold labeled anti-influenza antibody, and a washing solution is then injected into the test device to wash the carrier.

D. Subsequently, a reaction occurred on the test device is observed to carry out identification and diagnosis to determine influenza virus infection and the type (A or B) of the influenza virus.

The conventional simplified diagnostic kit for inspecting influenza infection is a simple examination tool, but with several disadvantages which should be improved.

More specifically, for carrying out the reaction of the diluted liquid specimen with the colloidal gold labeled antibody, an operator should drop the colloidal gold labeled antibody solution into the diluted liquid specimen as described above, so that complicated operations such as transfer from the first container to second container can be required. In addition, the amounts of the droplets of the colloidal gold labeled antibody solution tend to vary due to differences among individuals of operators, so that there is a difficulty in reproducibility of test results. Besides, the colloidal gold labeled antibody solution tends to aggregate alone depending on the temperature thereof, so that it may not pass through the filter cap. In addition, the colloidal gold labeled antibody is not washed and filtered, and may remain on the test device during the examination. Thus, the colloidal gold labeled antibody may color the whole carrier or be non-specifically bound to the antibody immobilized on the carrier, causing false coloration which tends to be a cause of being judged false positive. Particularly, in the case of under the low-temperature conditions or of a lean solution, the long-term storage more than one year will be speculated difficult.

As can be found in the above exemplified diagnostic kit for influenza virus infection, many of simplified diagnostic kits commercially available in the market, on which immunological examination methods is applied, adopt the process of mixing a diluted liquid specimen with a labeled antibody solution and forming an immunocomplex. Therefore, the points that should be improved in the diagnostic kits for inspecting influenza virus infection may directly correspond to those of the general simplified diagnostic kits commercially available in the market.

More specifically, in order to make a specimen and a labeled antibody react in the conventional diagnostic kits on the market, it is necessary to mix the diluted liquid specimen with a labeled antibody solution. In many cases, a method that an operator drops several droplets of the labeled antibody solution to the diluted liquid specimen has been adopted. In this method, however, the amounts of the droplets of the labeled antibody solution tend to vary due to differences among individuals of operators. For instance, comparing between the cases of dropping one droplet and three droplets, the amounts of the solutions dropped will be much different from each other. If the amount of the labeled antibody solution dropped is small, a sufficient reaction cannot occur because of insufficient sensitivity. If the amount of the solution dropped is large, in the examination results errors due to the amount of droplet of the labeled antibody easily occur because of an increase in probability of causing a non-specific reaction or the like. Besides, there is a possibility of being difficult in correct measurement if the labeled antibody is stored for a long period in liquid form as it is. Therefore, the present invention tends to solve all of the problems of the conventional examination methods and tools.

In addition, the description in "Influenza Diagnostic Manual" edited by Minoru Kanazawa and Norio Sugaya (first printing, published on Feb. 20, 2001, Nankodo, Co., Ltd. pages 110-115) of a non-patent document will serve as a reference.

DISCLOSURE OF THE INVENTION

Considering the above circumstances, a first object of the present invention is to provide, in an immunological examination method using an antigen-antibody reaction, an examination method having a small effect of individual differences among operators, preventing the generation of a nonspecific reaction, and having high reproducibility of diagnostic results and preservation stability of a test reagent; and a specimen container to be used in such an examination method. In addition, a second object of the present invention is to provide, in an examination method for inspecting influenza virus infection, an examination method having a small effect of individual differences among operators, preventing the generation of a nonspecific reaction, and having high reproducibility of diagnostic results and preservation stability of a test reagent; and a specimen container to be used in such an examination method. Furthermore, a third object of the present invention is to provide, in a simplified diagnostic kit on which an immunological examination method is applied, an examination method, which allow the usage of the kit more simply, having a small effect of individual differences among operators, preventing the generation of a nonspecific reaction, and having high reproducibility of diagnostic results and preservation stability of a test reagent; and a specimen container to be used in such an examination method.

To solve the problems described above, the invention according to claim 1 relates to a method of immunologically examining a specimen, comprising: attaching a cap having a built-in filter impregnated with a labeled antibody to a container body that houses a diluted liquid specimen; introducing the diluted liquid specimen from the container to a test device and observing a reaction; and determining the presence or absence of an analyte in the specimen.

The invention according to claim 2 of the present invention relates to the method according to claim 1, wherein the labeled antibody is a colloidal gold labeled antibody.

The invention according to claim 3 of the present invention relates to the method according to claim 1 or 2, wherein the analyte in the specimen is influenza virus.

The invention according to claim 4 of the present invention relates to the method according to any one of claims 1 to 3, further comprising using the method for reacting the specimen with the labeled antibody in a simple diagnostic kit.

The invention according to claim 5 of the present invention relates to a specimen container to be used in the examination method according to any one of claims 1 to 4, comprising a cap having a built-in filter impregnated with a labeled antibody which is attached to a container body that is to house a diluted liquid specimen.

The invention according to claim 6 of the present invention relates to the specimen container according to claim 5, wherein the labeled antibody is a colloidal gold labeled antibody.

The invention according to claim 7 of the present invention relates to the specimen container according to claim 5 or 6, wherein the analyte in the specimen is influenza virus.

The invention according to claim 8 of the present invention relates to the specimen container according to any one of claims 5 to 7, wherein the container is used as a component of a simplified diagnostic kit.

BRIEF DESCRIPTION OF THE DRAWINGS

In FIG. 1, reference numeral 1 denotes a container body of the specimen container, 11 denotes a diluted liquid specimen, and 12 denotes an open end portion of the container, respectively. In addition, reference symbol 1A denotes influenza A virus antigen and 1B denotes an influenza B virus antigen. Furthermore, reference numeral 2 denotes a cap, 21 denotes a filter impregnated with colloidal gold labeled antibody, 22 and 23 denote other filters, 24 denotes a fitting portion of the cap, 25 denotes a nozzle portion of the cap, and 3 denotes the specimen container equipped with the cap on the container body. Furthermore, reference numeral 4 denotes a test device, 41 denotes an opening portion thereof, and 42 denotes a surface thereof, respectively.

BEST MODE FOR CARRYING OUT THE INVENTION

Figure 1:
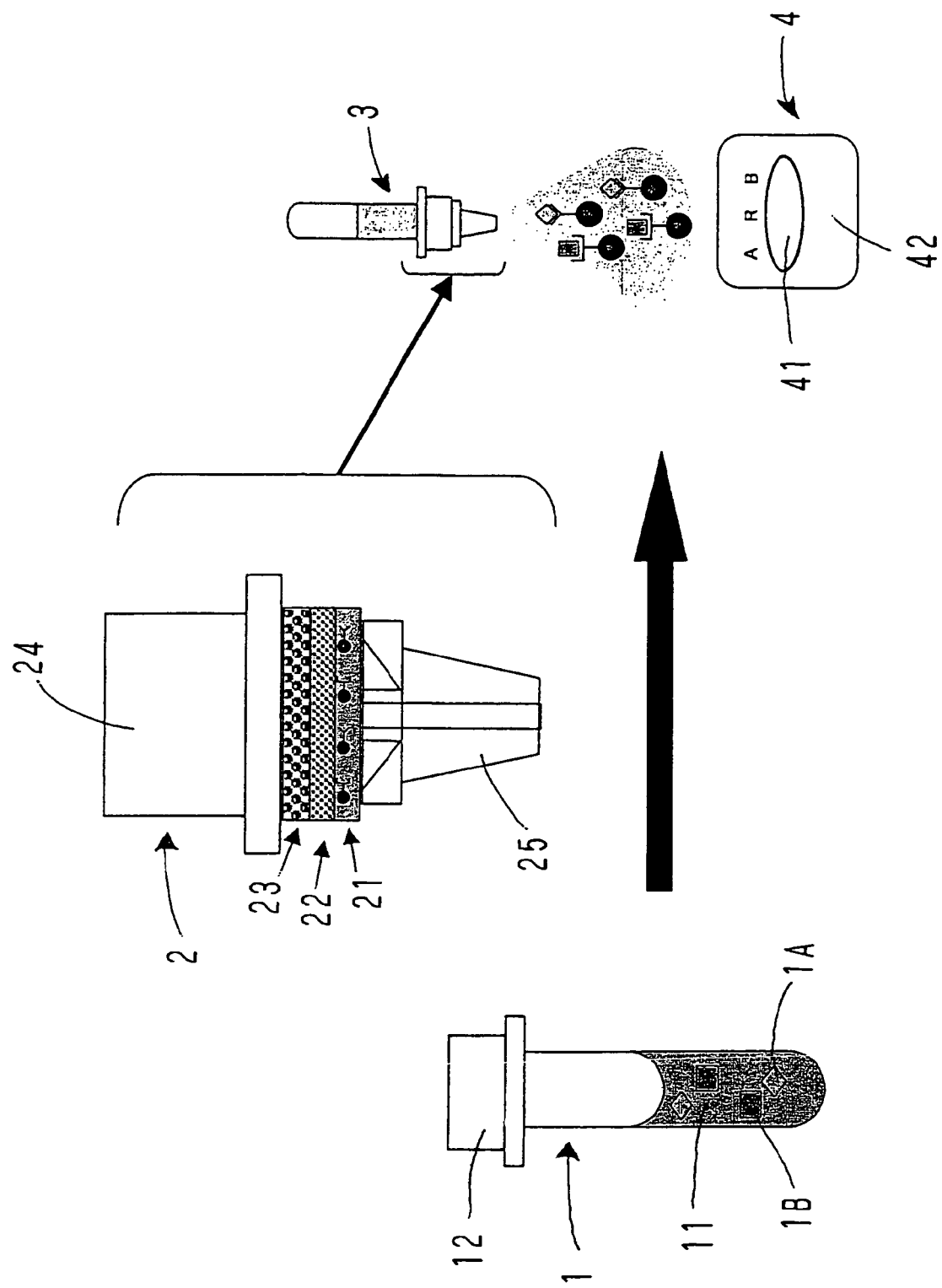
FIG. 1 is a schematic diagram of an exemplified method of examining a specimen and an exemplified specimen container to be used in such an examination method according to the present invention.

According to the present invention, as a method of bringing a specimen into contact with a labeled antibody, instead of mixing a diluted liquid specimen with a labeled antibody solution by using a method of dropping the labeled antibody solution in the conventional way, there is adopted a method of preparing a filter impregnated with a labeled antibody, installing the filter into a cap, and attaching the cap to a container body that houses a diluted liquid specimen to bring the specimen in the diluted liquid specimen into contact with the labeled antibody made to have impregnated in the filter to form an immunocomplex when the diluted liquid specimen is injected into a test device through the filter of the cap. The filter may be a member generally used as filter cloth or filter paper such as high-density polyethylene polymer filter cloth, glass fiber-based filter paper, and cellulose-based filter paper.

Furthermore, in the present invention, the term "cap" means at least one which can be attached on a container body filled with or housing a diluted liquid specimen or the like and one having a structure capable of passing liquid through and having a filter installed therein. The shape of cap may be selected a desired form such as a conical, a disk, a combination of tubular and conical or the like.

In the present invention, as a method of impregnating the filter with the labeled antibody, any method such as a method of dipping a filter member (filter cloth or filter paper) in a labeled antibody solution or alternatively a method of coating with or dropping the labeled antibody solution on the member may be adopted. For the industrial production of the filter, a certain amount of the solution may be applied using a coater. An example of how to make the filter impregnated with the labeled antibody will be now described as follows. A labeled antibody solution is sufficiently dropped on a proper filter cloth or proper filter paper, which has been cut into a same shape and size as those of the inside of a cap to be attached to the main body of a container that houses a diluted liquid specimen, to impregnate the filter with the solution, followed by drying at 35 to 38° C. for 30 to 40 minutes. Alternatively, it may be naturally dried at normal temperature.

The filter impregnated with the labeled antibody may be installed in the cap in any manner. A multi-layer structure, which is formed by making a combination of the filter impregnated with the labeled antibody and other filters, for instance, which from the nozzle side (discharge opening side) of the cap, a filter comprising a glass fiber-based filter paper impregnated with labeled antibody, a filter comprising another glass fiber-based filter paper, and a filter comprising high density polyethylene polymer filter cloth are laminated in that order, maybe installed in the cap.

In the present invention, as coloring material for labeling antibody, any material such as enzyme, noble metal colloid, pigment, and stained latex can be used. Of those, particles of noble metal colloid may be used preferably. Of the particles of the noble metal colloid, in particular, it is preferable to use colloidal gold particles prepared by a metal colloid preparation method which has been well known in the art.

Hereinafter, a method of examining a specimen and a specimen container to be used in such an examination method according to the present invention will be described more with reference to the drawing.

FIG. 1 is a schematic diagram for explaining a method of examining influenza virus and a specimen container to be used in the examination method as an example of the present invention. In FIG. 1, reference numeral 1 denotes a plastic container body containing a diluted liquid specimen 11, which has a test tube form. The diluted liquid specimen 11 is prepared such that a specimen collected from the nasal discharge of a patient, which contains influenza A virus antigen 1A (represented by a diamond shape) and influenza B virus antigen 1B (represented by a square shape), is prepared in a buffer solution with the addition of a surfactant and the like.

In FIG. 1, reference numeral 2 denotes a plastic cap having a fitting portion 24, which fits in an open end portion 12 of a container body 1, and a nozzle portion 25. On the waist portion of the cap 2, from the near side of the nozzle portion 25, a filter 21 prepared by impregnating glass-fiber filter paper with colloidal gold labeled antibody, a filter 22 comprising a glass fiber filter paper, and a filter 23 comprising a high density polyethylene polymer filter cloth are loaded in that order to build in a three-layered structure (in the figure, black circles in the filter 21 represent gold colloids, and the process of preparing the colloidal gold labeled antibody solution or the like is explained in Example 1 described latter).

Reference numeral 3 represents the status of making a specimen container by fitting the cap 2 to the container body 1 which houses the diluted liquid specimen 11. Reference numeral 4 denotes a plastic test device having an opening portion 41 formed in the surface thereof. In the test device, from the bottom side, absorbent cotton, absorbent paper, and a membrane on which influenza A and B viruses are immobilized, are housed in this order. The diluted liquid specimen 11 is placed in the specimen container 3 and left to stand for approximately 5 minutes and the total amount thereof is then dropped from a nozzle portion 25 of the cap 2 to the opening portion 41 of the test device 4. Subsequently, the membrane is washed with a washing solution and then subjected to a visual observation to investigate the status of spots generated in the opening portion 41 and to conduct diagnosis on the influenza virus infection, and the like.

EXAMPLES

Hereinafter, the present invention will be described in more detail with reference to examples. In the description below, reference numerals corresponding to the description of FIG. 1 are represented in [ ] (brackets), respectively.

Example 1

<Method of Examining the Influenza Virus Infection in Accordance with the Present Invention>

1. Preparation of Test Reagents (1) Preparation of Antibody-Immobilized Membrane 1-μL of each of a mouse-anti-influenza A virus antibody solution (A), a mouse-anti-influenza B virus antibody solution (B), and an anti-mouse IgG antibody solution (R) was independently dropped on a nitrocellulose membrane (60 μm in pore size) in the arrangement as shown in FIG. 1, respectively, and then dried. Consequently, three different antibodies were immobilized as spots of about 2 mm in diameter on the membrane. Furthermore, the membrane was subjected to a blocking treatment with a Tris-HCl buffer (pH 7.4) containing 0.1% MALIALIM AFB-1521 (manufactured by NOF CORPORATION) and 2.5% sucrose to prepare an antibody-immobilized membrane.

(2) Production of Test Device

As shown in FIG. 1, in a plastic case [42] provided with an opening portion [41] on the surface thereof for the addition of a diluted liquid specimen, absorbent cotton, absorbent cotton paper, and the antibody-immobilized membrane were laminated in that order from the bottom such that three immobilized antibodies were arranged in the vicinity of the middle of the opening portion to provide a test device [4].

Furthermore, as shown in FIG. 1, the alphabetical letters A, R, and B represented on the test device [4] designate the regions on which the mouse-anti-influenza A virus antibody solution, the anti-mouse IgG antibody solution, and the mouse-anti-influenza B virus antibody solution were immobilized in spots, respectively.

(3) Preparation of Labeled Antibody

A hydrogen tetrachloroaurate (III) aqueous solution and a trisodium citrate aqueous solution were added to boiled distilled water and then heated while stirring. Subsequently, the mixture was cooled in ice water, producing gold colloid. The gold colloid has a particle size of approximately 60 nm. The resulting gold colloid was mixed with the mouse-anti-influenza A virus antibody and mouse-anti-influenza B virus antibody (which recognize other epitopes different from the antibodies immobilized on the nitrocellulose membrane, respectively) in a boric acid buffer (pH 9.0), followed by stirring at room temperature to provided labeled antibody. The mixture was further subjected to a blocking treatment by the addition of a 10% BSA aqueous solution and then precipitated by centrifugation, resulting in two kinds of colloidal gold labeled antibodies.

(4) Preparation of Labeled-Antibody Solution

Two different colloidal gold labeled antibodies were suspended together in PBS containing 0.2% Tween 20, 1.0% sucrose, and 0.2% BSA, thereby preparing a colloidal gold labeled antibody solution containing both a colloidal gold labeled antibody for influenza A virus and a colloidal gold labeled antibody for influenza B virus.

(5) Preparation of Filter Impregnated with Labeled Antibody

From members listed in Table 1, glass fiber-based filter paper FO75-14 was selected and then cut into disk-shaped sections (7.5 mm in diameter) so as to fit to the shape and size of the inside of the cap. On each of the disk-shaped sections, 60 μL of the colloidal gold labeled antibody solution was dropped and then dried naturally, thereby preparing a filter [21] impregnated with the colloidal gold labeled antibody.

(6) Preparation of Cap Having Built-In Filter Impregnated with Labeled Antibody

As shown in FIG. 1, from the side of supplying the diluted liquid specimen, a filter constructed of high-density polyethylene polymer filter cloth [23], a filter constructed of glass fiber-based filter paper [22], and a filter impregnated with the colloidal gold labeled antibody [21] were stacked in this order and housed in the cap [2], thereby preparing a cap having a built-in filter impregnated with the colloidal gold labeled antibody (hereinafter, referred to as "cap of the present invention"). As shown in FIG. 1, the resulting cap of the present invention was attached to the container body [1] which housed the diluted liquid specimen [11] and used.

2. Method of Detecting Virus (1) Dilute Solution

PBS (pH 7.4) containing 2% BSA was used.

(2) Washing Solution

PBS (pH 7.4) containing 12% urea was used.

(3) Detection Procedure

A. Diluted liquid specimens containing purified influenza antigen (Type A virus: originated from the strain Kitakyushu/159/93, Type B virus: originated from Lee/40 strain) were prepared by adding each virus into the dilute solution so that the virus concentration is from $2 \times 10^6$ to $1 \times 10^5$ at a $TCID_{50}$/test unit, respectively.

B. The diluted liquid specimen containing nasal discharge was prepared by putting the cotton body which collected nasal discharge in a container with 1.2 mL of diluted liquid specimen and allowing the nasal discharge components to be eluted in the diluted liquid specimen.

C. The cap [2] of the present invention was attached to the container body [1] containing 1.2 mL of the diluted liquid specimen containing the purified influenza antigen or nasal discharge specimen that was prepared in the above steps A or B, respectively, and the whole amount thereof was then dropped in the opening portion [41] of the test device [4].

D. After the diluted liquid specimen [11] was not found on the antibody-immobilized membrane, 500 μL of washing liquid was dropped in the opening portion and the antibody-immobilized membrane was then washed.

E. The antibody-immobilized membrane after washing was subjected to a visual observation and investigated the presence or absence of red detection spots. The concrete judgments were evaluated by the following four criteria. When the red detection spots were observed, then the results were rated by following two different criteria depending to the intensity thereof, i.e., + (positive) and ++ (more positive). And when the detected spot was not clear, it could be rated by ± (indeterminant). When the detection spot was not observed, it could be rated by − (negative).

Test Examples

Hereinafter, the present invention will be further described with reference to the test examples.

Test Example 1

<Selecting Test for Members>

(1) Test Procedure

The cap of the present invention was prepared by the method of Example 1 using members listed in Table 1. The cap of the present invention attached to the container body in which 1.2 mL of a diluted liquid specimen containing neither the influenza purification antigen nor nasal discharge, followed by dropping the whole amount thereof in a test tube. From the absorbance of the resulting filtrate at a wavelength of 537 nm, the amount of the colloidal gold labeled antibody in the filtrate was calculated and then compared with the amount of the colloidal gold labeled antibody with which the filter had been impregnated to obtain the recovery rate. The results of the test are shown in Table 1.

(2) Test Results

The test results are shown in Table 1.

TABLE 1

| Filtration filter | Brand name (Company name) | Thickness of filter (mm) | Pore size (μm) | Recovery rate (%) |
|---|---|---|---|---|
| High density polyethylene polymer | LG20 (Flon Industry Co., Ltd.) | 1.9 | 20 | 96.7 |
| Glass fiber-based filter paper | F075-14 (Advantec MFS Inc.) | 0.355 | 23 | 95.4 |
| Glass fiber-based filter paper | GB-140 (Advantec MFS Inc.) | 0.56 | 0.4 | 71.2 |
| Cellulose-based filter paper | 17 chr (Whatman Japan KK) | 0.92 | Not represented | 57.7 |

(3) Discussion

From Table 1, according to the method of the present example, on the basis of the recovery rate of the colloidal gold labeled antibody, it was revealed that a member (filter cloth or filter paper) which could be used in the production of a filter impregnated with labeled antibody in consideration of the size of the labeled antibody, the amount of the labeled antibody with which the filter was impregnated, and the raw material and thickness of the filter, and the like, can be properly selected.

Test Example 2

<Confirmatory Test on Basic Characteristics>

(1) Test Procedure

A cap of the present invention was prepared using LG20 as a filter member and then attached to the container body in which 1.2 mL of diluted liquid specimens containing purified influenza antigens (Types A and B) having concentrations shown in Table 2 were contained, and the test according to the method of Example 1 was carried out. As a control method, the following test was carried out. Specifically, the container body in which a diluted liquid specimen containing the purified influenza antigen was further added with 60 μL of a colloidal gold labeled antibody solution. Subsequently, a filter impregnated with the labeled antibody which was housed in the cap of the present invention was replaced with a filter not impregnated with the labeled antibody, followed by conducting the test. The test results are shown in Table 2.

(2) Test Results

Test results are shown in Table 2.

(3) Discussion

From Table 2, it was confirmed that no difference in the test accuracy has been found between the method of the present invention (the method of dropping the diluted liquid specimen from the filter impregnated with the labeled antibody) and the control method (the conventional method of mixing the diluted liquid specimen and the labeled antibody solution). Therefore, it was proved that the method of the present invention has the same performance as the control one.

TABLE 2

| | Amount of virus | | | | | |
|---|---|---|---|---|---|---|
| | $2 \times 10^6$ | $8 \times 10^5$ | $4 \times 10^5$ | $2 \times 10^5$ | $1 \times 10^5$ | Blank |
| a. Detection of influenza A virus | | | | | | |
| Method of the invention | ++ | ++ | ++ | + | + | − |
| Control method | ++ | ++ | ++ | + | + | − |
| b. Detection of influenza B virus | | | | | | |
| Method of the invention | ++ | ++ | ++ | + | + | − |
| Control method | ++ | ++ | ++ | + | + | − |

(The amount of virus was represented by unit of "$TCID_{50}$/test")

Test Example 3

<Confirmatory Test for Effects of Method of Present Invention>

(1) Test Procedure

LG20 was used as a filtration filter member and the amount of the colloidal gold labeled antibody solution with which the filter was impregnated was varied as shown in Table 3 to prepare the cap of the present invention. The cap of the present invention was attached to a container body that housed 1.2 mL of a diluted liquid specimen containing a nasal discharge specimen (negative specimen) which the nonexistence of influenza A virus or influenza B virus was confirmed by the PCR method. Subsequently, the examination was carried out according to the method of Example 1. As a control method, 1 to 3 droplets of the colloidal gold labeled antibody solution were dropped from a dropping bottle to the container body in which a diluted liquid specimen containing the purified influenza antigen and then a filter impregnated with the labeled antibody housed in the cap of the invention was replaced with a filter not impregnated with the labeled antibody, and then the test was carried out after attaching the cap. The results of the test are shown in Table 3.

(2) Test Results

Test results are listed in Table 3.

TABLE 3

| | Number of specimen determined as "+" among 20 specimen | | |
|---|---|---|---|
| | | Negative specimen | |
| | | Type A | Type B |
| Control method | 1 drop (corresponding to 30 μL) | 0/20 | 0/20 |
| | 2 drops (corresponding to 60 μL) | 0/20 | 0/20 |
| | 3 drops (corresponding to 90 μL) | 1/20 | 1/20 |
| Method of the invention | impregnated with 54 μL | 0/20 | 0/20 |
| | impregnated with 60 μL | 0/20 | 0/20 |
| | impregnated with 66 μL | 0/20 | 0/20 |

(3) Discussion

From Table 3, when 3 droplets of the labeled antibody solution were dropped, it was confirmed that the specimen causing a non-specific reaction was present. In contrast, in the method of the present invention, the amount of the labeled antibody was constant, therefore a non-specific reaction could not be observed in the specimen. From this test results, it was confirmed that according to the present invention, the detection errors due to the amount of labeled antibody could be resolved.

Test Example 4

<Confirmatory Test 1 for Preservation Stability of Labeled Antibody Solution>

(1) Test Procedure

LG20 was used as a filter member and caps of the present invention were then prepared according to Example 1, and stored at 30° C. (30% in humidity) or 37° C. (30% in humidity). Each of the caps at time periods of zero month, 6 months, and 9 months from the start of storage were attached to the container body that housed 1.2 mL of a diluted sample solution (diluted sample solution containing $2 \times 10^6$ on the basis of virus $TCID_{50}$/test unit for each virus) containing the purified influenza antigen (A-type virus: originated from the strain Kitakyusyu/159/93, B-type virus: from the strain Lee/40), followed by carrying out the test according to the method of Example 1. As a control method, 3 droplets of each of the colloidal gold labeled antibody solutions stored at 30° C. (30% in humidity) or 37° C. (30% in humidity) for zero month, 6 months, and 9 months were dropped from a dropping bottle to the container body that housed a diluted liquid specimen containing the purified influenza antigen. Subsequently, the container was attached with a cap having a filter not impregnated with the labeled antibody instead of the filter impregnated with the labeled antibody housed in the cap of the invention, followed by carrying out the test. The results of the test are shown in Table 4.

(2) Test Results

The test results are shown in Table 4.

(3) Discussion

As shown in Table 4, it was confirmed that when the labeled antibody was stored at 37° C. (30% in humidity), it was impossible to conduct the correct measurement of the storage sample in the solution state for 6 months, while the filter made by the preset invention was capable of carrying out a correct measurement even after the 9-month storage.

TABLE 4

| Storage temperature | | Storage period | | | | | |
|---|---|---|---|---|---|---|---|
| | | 0 month | | 6 months | | 9 months | |
| | | Purified influenza antigen | | | | | |
| | | Type A | Type B | Type A | Type B | Type A | Type B |
| 37° C. | Control method | + | + | ± | ± | − | − |
| | Method of the invention | + | + | + | + | + | + |
| 30° C. | Control method | + | + | + | + | + | + |
| | Method of the invention | + | + | + | + | + | + |

Test Example 5

<Confirmatory Test 2 for Preservation Stability of Labeled Antibody Solution>

(1) Test Procedure

LG20 was used as a filter member and caps of the present invention were then prepared according to Example 1. A dropping bottle containing the cap of the invention and the colloidal gold labeled antibody solution was placed together with a desiccant in an air-tight container and then stored for whole day and night at −30° C. The cap was thawed to room temperature and then attached to a container body that housed 1.2 mL of a diluted liquid specimen containing a nasal discharge specimen (negative specimen), in which the absence of influenza A virus and influenza B virus was confirmed by the PCR method, or a diluted liquid specimen of influenza-purified antigen (A-type virus: originated from the strain Kitakyusyu/159/93, B-type virus: originated from the strain Lee/40, each virus was contained 2×10$^6$ with TCID$_{50}$/test unit), followed by carrying out the test according to the method of Example 1. As a control method, 2 droplets of the colloidal gold labeled antibody solution thawed to room temperature was dropped in the container body that housed a diluted liquid specimen containing a negative specimen or a purified influenza antibody. Subsequently, the container was attached with a cap having a filter not impregnated with the labeled antibody instead of the filter impregnated with the labeled antibody housed in the cap of the present invention, followed by carrying out the test. As a standard method, instead of the colloidal gold labeled antibody solution stored at −30° C., a colloidal gold labeled antibody solution stored at room temperature was used and a test was then carried out by the same procedures as those of the above control method. The test results are shown in Table 5.

(2) Test Results

Test results are shown in Table 5.

TABLE 5

| Storage temperature | | Negative specimen | | | Purified-influenza antigen | | |
|---|---|---|---|---|---|---|---|
| | | Type A | Type B | R part | Type A | Type B | R part |
| −30° C. | Control method | + | + | + | + | + | + |
| | Method of the invention | − | − | ++ | ++ | ++ | ++ |
| Room temperature | Standard method | − | − | ++ | ++ | ++ | ++ |

(3) Discussion

At first, in the control method in which the colloidal gold labeled antibody solution was used after storing at −30° C., the cap, which the filter impregnated with the labeled antibody housed in the cap of the invention was replaced with the filter not impregnated with labeled antibody, was colored with red when dropping a mixture of the colloidal gold labeled antibody solution and the diluted liquid specimen to the opening portion of the test device. Thus, it was confirmed that the colloidal gold labeled antibody was captured by the filter. Next, in the control method, the R region showed coloration of "+" instead of its normal coloration of "++". Besides, even the negative specimen, which no coloration should not be observed essentially, showed a coloration of "+". It has been considered that aggregation of the colloidal gold labeled antibody was caused and a non-specific reaction was occurred if the colloidal gold labeled antibody solution is stored −30° C. In contrast, it revealed that in the method of the present invention, the same results as those of the standard method were obtained and no influence of storage occurred even at a storage temperature of −30° C.

In this way, as is evident from Test Examples 4 and 5, the cap of the present invention shows an excellent stability in storage of the labeled antibody, so that there is no need to strictly control the temperature during transportation and the like.

INDUSTRIAL APPLICABILITY

As described above, according to the method of examining a specimen of the present invention, the cap having a built-in filter impregnated with labeled antibody is attached to the container body that houses a diluted liquid specimen, and the diluted liquid specimen is injected from the container to a test device, followed by observing a reaction occurred therein. Therefore, in contrast to the conventional examination, there is no need to drop the labeled antibody solution into the diluted liquid specimen. Besides, there is no need to transfer the diluted liquid specimen from the first container to the second container. In other words, the method of the invention is a very simple examination method. In addition, there is no need to drop a labeled antibody solution to the diluted liquid specimen, the occurrence of errors due to the amount of the labeled antibody solution dropped can be prevented. That is, the insufficiency of the reaction and the generation of the non-specific reaction due to the individual differences in the amount dropped can be eliminated resulting in an increase in examination accuracy. Furthermore, according to the examination method of the present invention, there is no need to store the labeled antibody in a solution state for a long term. Therefore, there is no need to consider the prevention of deterioration of the labeled antibody solution.

Furthermore, the specimen container of the present invention is constructed such that a cap having a built-in filter impregnated with labeled antibody is attached to a container body for housing a diluted liquid specimen. Therefore, the container can be easily operated even though it has an extremely simple structure. Besides, the examination accuracy does not vary depending on operator individuals. Therefore, it will be most applicable to components for a simplified diagnostic kit of a specimen applying an immune reaction.

Consequently, the method of examining a specimen and a specimen container to be used in the examination method can be applied to the examination and diagnosis of various symptoms such as the infection by virus, e.g., influenza virus, and a pregnancy status.

The invention claimed is:

1. A method for immunologically examining a specimen, comprising the steps of:
   attaching a cap having a built-in filter impregnated with a labeled antibody to a container body that houses a diluted liquid specimen;
   dispensing the diluted liquid specimen from the container through the built-in filter of the cap so as to react the diluted liquid specimen and the impregnated labeled antibody;
   introducing the dispensed diluted liquid specimen to a test device and observing a reaction; and
   determining a presence or absence of an analyte in the specimen.

2. The method according to claim 1, wherein the labeled antibody is a colloidal gold labeled antibody.

3. The method according to claim 1, wherein the analyte in the specimen is influenza virus.

4. A specimen container to be used in the examination method according to any one of claims 1 to 3, comprising a cap having a built-in, flow-through filter impregnated with a labeled antibody which is attached to a container body that is to house a diluted liquid specimen.

5. The specimen container according to claim 4, wherein the labeled antibody is a colloidal gold labeled antibody.

6. The specimen container according to claim 4, wherein the analyte in the specimen is influenza virus.

7. The specimen container according to claim 4, wherein the container is used as a component of a simplified diagnostic kit.

* * * * *